(12) United States Patent
Okamoto et al.

(10) Patent No.: US 11,679,242 B2
(45) Date of Patent: Jun. 20, 2023

(54) BALLOON CATHETER

(71) Applicant: GOODMAN CO., LTD., Aichi (JP)

(72) Inventors: Mitsumasa Okamoto, Aichi (JP); Takashi Kunisada, Aichi (JP)

(73) Assignee: GOODMAN CO., LTD., Aichi (JP)

( * ) Notice: Subject to any disclaimer, the term of this patent is extended or adjusted under 35 U.S.C. 154(b) by 0 days.

(21) Appl. No.: 17/137,638

(22) Filed: Dec. 30, 2020

(65) Prior Publication Data

US 2021/0113821 A1 Apr. 22, 2021

Related U.S. Application Data

(63) Continuation of application No. PCT/JP2019/023089, filed on Jun. 11, 2019.

(30) Foreign Application Priority Data

Jul. 9, 2018 (JP) .............................. JP2018-130088

(51) Int. Cl.
*A61M 25/10* (2013.01)
*A61B 17/22* (2006.01)

(52) U.S. Cl.
CPC ........... *A61M 25/104* (2013.01); *A61B 17/22* (2013.01); *A61M 25/1002* (2013.01); *A61B 2017/22001* (2013.01); *A61B 2017/22065* (2013.01); *A61M 2025/109* (2013.01); *A61M 2025/1081* (2013.01); *A61M 2025/1086* (2013.01); *A61M 2205/0216* (2013.01)

(58) Field of Classification Search
CPC ............ A61M 25/104; A61M 25/1002; A61M 25/005; A61M 2025/1084–109; A61B 17/22; A61B 2017/22001; A61B 2017/22051; A61F 2002/9586; A61F 2002/9583
USPC ........................................................ 606/159
See application file for complete search history.

(56) References Cited

U.S. PATENT DOCUMENTS 4,796,629 A * 1/1989 Grayzel .............. A61M 25/104
604/103.09
5,196,024 A * 3/1993 Barath ........... A61B 17/320725
604/103.07

(Continued)

FOREIGN PATENT DOCUMENTS

CN 107206218 A 9/2017
EP 2990069 A1 * 3/2016 ............. A61F 2/958

(Continued)

OTHER PUBLICATIONS

International Search Report issued in International Application No. PCT/JP2019/023089, dated Jul. 23, 2019 (4 pages).

(Continued)

*Primary Examiner* — Kathleen S Holwerda
*Assistant Examiner* — Serenity A Miller
(74) *Attorney, Agent, or Firm* — Osha Bergman Watanabe & Burton LLP

(57) ABSTRACT

A balloon catheter includes a balloon that is formed of film and includes an inflation/deflation portion. The inflation/deflation portion includes a plurality of linear projections that projects in a thickness direction of the film and extends along a surface of the film. One of the linear projections is an inner projection that projects inside the balloon.

3 Claims, 4 Drawing Sheets

(56) References Cited

U.S. PATENT DOCUMENTS

| | | | | |
|---|---|---|---|---|
| 5,458,572 | A | * | 10/1995 | Campbell ........... A61M 25/104 604/103.08 |
| 6,013,055 | A | * | 1/2000 | Bampos ............ A61M 25/1002 604/103.07 |
| 6,652,485 | B1 | * | 11/2003 | Gaudoin ........... A61M 25/1029 604/103.07 |
| 2004/0138691 | A1 | | 7/2004 | Goodin et al. |
| 2005/0038383 | A1 | * | 2/2005 | Kelley ........... A61B 17/320725 606/159 |
| 2011/0160756 | A1 | | 6/2011 | Aggerholm et al. |
| 2012/0130407 | A1 | | 5/2012 | Aggerholm et al. |
| 2015/0150586 | A1 | | 6/2015 | Aggerholm et al. |
| 2015/0360007 | A1 | | 12/2015 | Schneider et al. |
| 2015/0360008 | A1 | * | 12/2015 | Schneider ............. A61M 25/10 604/103.07 |
| 2016/0058982 | A1 | | 3/2016 | Aggerholm et al. |
| 2016/0128718 | A1 | | 5/2016 | Aggerholm et al. |
| 2018/0043141 | A1 | | 2/2018 | Sano et al. |
| 2020/0179662 | A1 | | 6/2020 | Sano et al. |

FOREIGN PATENT DOCUMENTS

| | | | |
|---|---|---|---|
| EP | 3115077 A1 | 1/2017 | |
| EP | 3157613 A1 | 4/2017 | |
| GB | 2532099 A * | 5/2016 | ..... A61B 17/320725 |
| JP | 2008-237844 A | 10/2008 | |
| JP | 2014-506140 A | 3/2014 | |
| JP | 2015-104671 A | 6/2015 | |
| JP | 2016-52452 A | 4/2016 | |
| JP | 2017-522078 A | 8/2017 | |
| WO | 2015195757 A1 | 12/2015 | |

OTHER PUBLICATIONS

International Search Report issued in International Application No. PCT/JP2019/023088, dated Jul. 23, 2019 (4 pages).
Office Action issued in corresponding Japanese Patent Application No. 2020-530043, dated Aug. 17, 2021 (7 pages).
Office Action issued in corresponding Japanese Patent Application No. 2020-530044, dated Aug. 17, 2021 (7 pages).
Extended European Search Report issued in the counterpart European Patent Application No. 19833984.8, dated Jun. 28, 2021 (7 pages).
Office Action issued in related Indian Patent Application No. 202017055896 dated Sep. 16, 2021 (5 pages).
Office Action issued in related Indian Patent Application No. 202017055895 dated Sep. 24, 2021 (5 pages).
Office Action issued in related Japanese Patent Application No. 2020-530043, dated Aug. 17, 2021 (7 pages).
International Preliminary Report on Patentability issued for PCT/JP2019/023089, dated Jan. 21, 2021 (13 pages).
International Preliminary Report on Patentability issued for PCT/JP2019/023088, dated Jan. 21, 2021 (11 pages).
Office Action issued in related Chinese Patent Application No. 201980035521.1 dated Dec. 24, 2021 (14 pages).
Office Action issued in related Chinese Patent Application No. 201980035516.0 dated Dec. 24, 2021 (14 pages).
Office Action issued in related Chinese Patent Application No. 201980035521.1 dated Jul. 25, 2022 (13 pages).
Office Action issued in related Chinese Patent Application No. 201980035516.0 dated Jul. 14, 2022 (14 pages).
Office Action issued in related Korean Patent Application No. 10-2020-7037568, dated Oct. 31, 2022, with translation (9 pages).
Office Action issued in corresponding Korean Patent Application No. 10-2020-7037569, dated Oct. 31, 2022, with translation (10 pages).
Rejection Decision issued in related Chinese Application No. 201980035521.1; dated Jan. 5, 2023 (12 pages).
Office Action issued in related Chinese Application No. 201980035516.0; dated Nov. 25, 2022 (13 pages).
Office Action issued in corresponding European Patent Application No. 19834109.1 dated Apr. 5, 2023 (6 pages).

* cited by examiner

BALLOON CATHETER

CROSS-REFERENCE TO RELATED APPLICATION

The present application is a continuation of PCT International Application No. PCT/JP2019/023089 filed on Jun. 11, 2019 which claims the benefit of priority from Japanese Patent Application No. 2018-130088 filed on Jul. 9, 2018, the entire contents of which are incorporated herein by reference.

BACKGROUND

Technical Field

The present invention relates to balloon catheter.

Description of the Related Art

A balloon catheter has been used for remedies such as PTA (percutaneous transluminal angioplasty) and PTCA (percutaneous transluminal coronary angioplasty), etc. (for example, see Patent Literature 1). The balloon catheter includes an inflatable and deflatable balloon on a tip-end side thereof. As for the balloon catheter, the balloon in a deflated state is introduced into a spot narrowed or obstructed by a lesion or the like generated in a blood vessel and then the spot is stretched by inflating the balloon.

PATENT LITERATURE

Patent Literature 1: Japanese Patent Laid-Open No. 2008-237844

As for the balloon catheter, the balloon is usually required to exhibit pressure resistance. Further, in a case where, for example, a lesion is hardened, a high pressure is assumed to be applied to the balloon to inflate the balloon. Accordingly, considering such a case, the balloon is required to exhibit a higher pressure resistance.

In this regard, to increase the pressure resistance of the balloon, it is necessary to increase the strength of the balloon. For example, the strength of the balloon is supposed to be increased by forming a projecting portion on an outer surface of the balloon. However, in such a case, the outer diameter of the balloon is increased, making it likely that the passability of the balloon in the body is decreased.

SUMMARY

One or more embodiments of the present invention provide a balloon catheter configured such that a balloon can be improved in pressure resistance with a decrease in the passability thereof in the body reduced.

A balloon catheter of one or more embodiments includes a balloon formed of a film with a predetermined thickness, the balloon including an inflation/deflation portion that is inflatable (i.e., inflatable and deflatable), in which the film is provided with a linear projection projecting in a thickness direction and extending along a surface of the film at the inflation/deflation portion, and an inner projection projecting inside the balloon in the thickness direction is provided as the projection.

According to one or more embodiments, the film, which forms the balloon, is provided with the linear projection at the inflation/deflation portion. The film can thus be reinforced at the inflation/deflation portion. Further, with an inner projection, which projects inside the balloon, provided as the projection, the film can be reinforced with an increase in the outer diameter of the balloon reduced by virtue of the inner projection. The balloon can thus be improved in pressure resistance with a decrease in the passability thereof in the body reduced.

In a balloon catheter of one or more embodiments, the inflation/deflation portion includes: a straight tube portion having a maximum diameter during inflation; and a pair of tapered portions provided on opposite sides across the straight tube portion in an axial direction of the balloon, the tapered portions each being reduced in diameter toward a side away from the straight tube portion, the film is provided with the projection at each of the straight tube portion and the tapered portions, an outer projection projecting outside the balloon is provided as the projection at the straight tube portion, and the inner projection is provided as the projection at at least either one of the tapered portions.

According to one or more embodiments, with the projection provided at each of the straight tube portion and the tapered portions of the inflation/deflation portion, the film can be reinforced substantially throughout the inflation/deflation portion. The pressure resistance of the balloon can thus be favorably increased.

Further, with the outer projection provided as the projection at the straight tube portion, the outer projection can be pressed against and dug into the blood vessel in the body during the inflation of the balloon. The outer projection can thus function as a slip resistance during the inflation of the balloon.

Further, with the inner projection provided as the projection at least either one of the tapered portions, an increase in an outer diameter of the tapered portion can be reduced. Thus, in the configuration where the balloon is added with a slip-resistance function, the pressure resistance of the balloon can be favorably increased with a decrease in the passability of the balloon reduced.

In a balloon catheter of one or more embodiments, the inner projection is provided at at least one on a tip-end side of the tapered portions (i.e., tip-end side tapered portion).

According to one or more embodiments, with the inner projection provided at one on the tip-end side of the balloon of the tapered portions, an increase in the outer diameter of the tapered portion on the tip-end side of the balloon can be reduced. Thus, a decrease in the passability can be favorably reduced in introducing the balloon into the body.

In a balloon catheter of one or more embodiments, the inner projection is provided at each of both the tapered portions.

According to one or more embodiments, with the inner projection provided at each of the tapered portions, an increase in the outer diameter of each of the tapered portions can be reduced. Thus, a decrease in the passability can be further reduced in introducing the balloon into the body. In addition, in this case, a decrease in the passability can also be favorably reduced in moving the balloon to the base-end side, such as pulling the balloon out of the body.

In a balloon catheter of one or more embodiments, the projection of the straight tube portion and the projection of each of the tapered portions all extend in the axial direction of the balloon along the surface of the film.

According to one or more embodiments, with the projection of the straight tube portion and the projection of each of the tapered portions all extending in the axial direction of the balloon along the surface of the film, the elongation of the balloon in the axial direction can be reduced during the inflation of the balloon (in particular, the inflation/deflation portion). Thus, a balloon length can be easily kept constant during the inflation of the balloon.

In a balloon catheter of one or more embodiments, the projection of the straight tube portion extends throughout the straight tube portion in the axial direction, the projection of each of the tapered portions extends throughout the tapered portion in the axial direction, and the projection of the straight tube portion and the projection of each of the tapered portions are provided at a same position in a circumferential direction of the balloon.

According to one or more embodiments, at each of the straight tube portion and the tapered portions, the projection extends therethroughout in the axial direction of the balloon. Further, the projections of the straight tube portion and the tapered portions are all provided at the same position in the circumferential direction of the balloon, so that the projections are continuously provided in series throughout the inflation/deflation portion in the axial direction. In this case, the elongation of the balloon in the axial direction can be further reduced during the inflation of the balloon and, consequently, the balloon length can be more easily kept constant during the inflation of the balloon.

BRIEF DESCRIPTION OF DRAWINGS

The above-described features and advantages of one or more embodiments the present invention will be further clarified by the following detailed description made with reference to the attached drawings.

DETAILED DESCRIPTION

Figure 1:
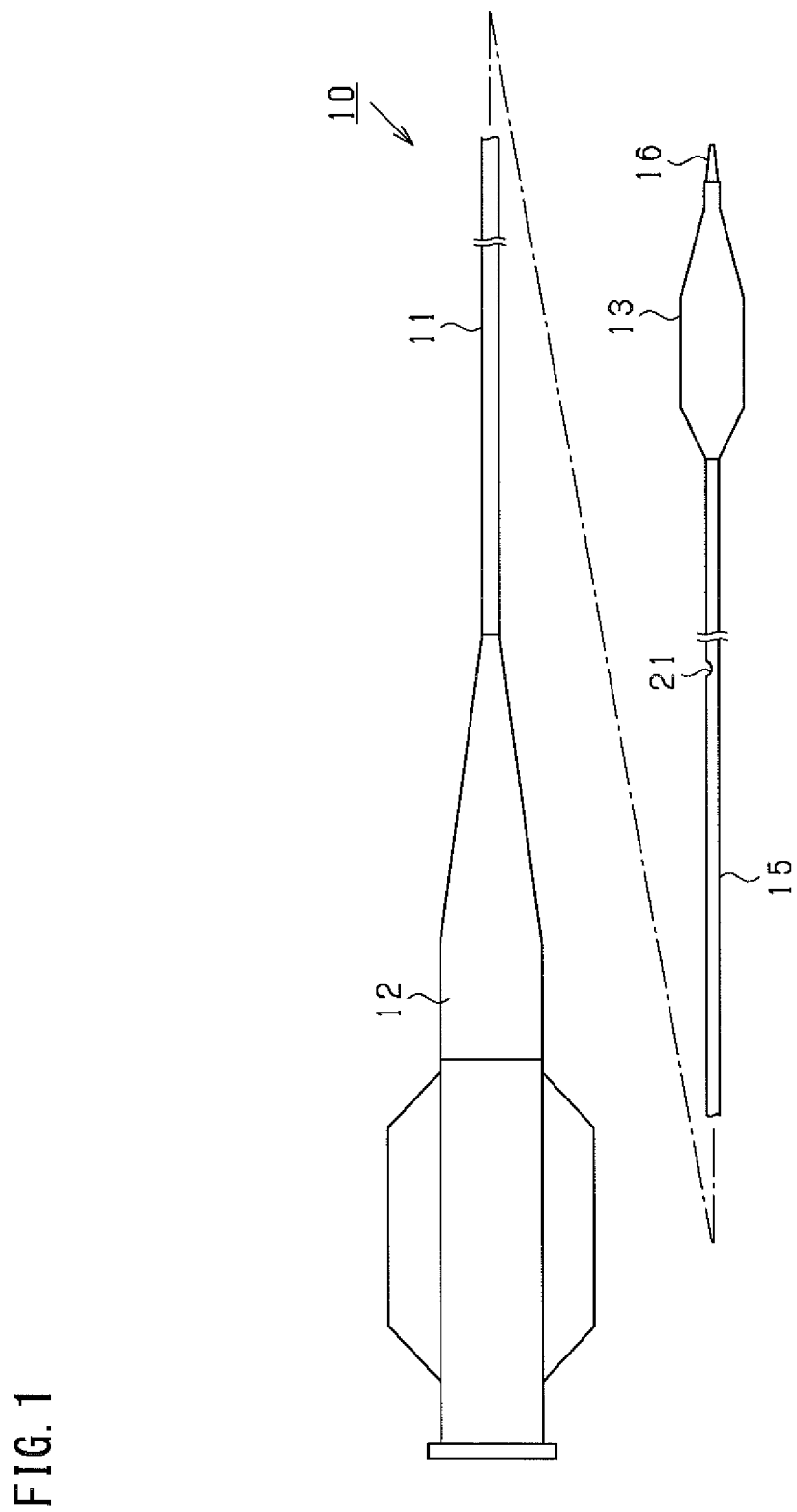
FIG. 1 is a schematic overall side view showing a configuration of a balloon catheter.

Description will be made below on embodiments of a balloon catheter on the basis of the drawings. First, an overall configuration of a balloon catheter 10 will be described with reference to FIG. 1. FIG. 1 is a schematic overall side view showing a configuration of the balloon catheter 10.

As shown in FIG. 1, the balloon catheter 10 includes a catheter body 11, a hub 12 attached to a base-end portion (proximal-end portion) of the catheter body 11, and a balloon 13 attached on a tip-end side (distal-end side) of the catheter body 11.

The catheter body 11 includes an outer tube 15 and an inner tube 16 inserted in the outer tube 15. The outer tube 15 is formed of a resin material; for example, it is formed of polyamide elastomer. A base-end portion of the outer tube 15 is bonded to the hub 12, while a tip-end portion thereof is bonded to the balloon 13. Further, the outer tube 15 has therein a lumen 15a (see FIG. 2) extending therethroughout in an axial direction thereof. The lumen 15a is in communication with the inside of the hub 12 while being in communication with the inside of the balloon 13.

It should be noted that the outer tube 15 may be formed by bonding a plurality of tubes aligned in the axial direction to each other. In this case, it is likely that, for example, one of the tubes on a base-end side is formed of a metal material such as a Ni—Ti alloy or stainless steel, while one on a tip-end side is formed of a resin material such as polyamide elastomer.

The inner tube 16 is formed of a resin material; for example, it is made of polyamide elastomer. The inner tube has therein a lumen 16a (see FIG. 2) extending therethroughout in an axial direction thereof. A base-end portion of the inner tube 16 is bonded at an axial middle position of the outer tube 15, while a part of a tip-end side thereof is extended on a tip-end side relative to the outer tube 15. Further, the balloon 13 is provided on the inner tube 16, externally covering such an extended region.

The lumen 15a of the outer tube 15 functions as a fluid lumen where a compressed fluid is to flow in inflating or deflating the balloon 13. Meanwhile, the lumen 16a of the inner tube 16 functions as a guide wire lumen where a guide wire G is to be inserted. A base-end opening 21 of the lumen 16a is present at an axial middle position of the balloon catheter 10. The present balloon catheter 10 is thus in the form of a so-called RX catheter. It should be noted that the base-end opening 21 of the lumen 16a may be included in a base-end portion of the balloon catheter 10. In this case, the balloon catheter 10 is in the form of a so-called over-the-wire catheter.

Figure 2:
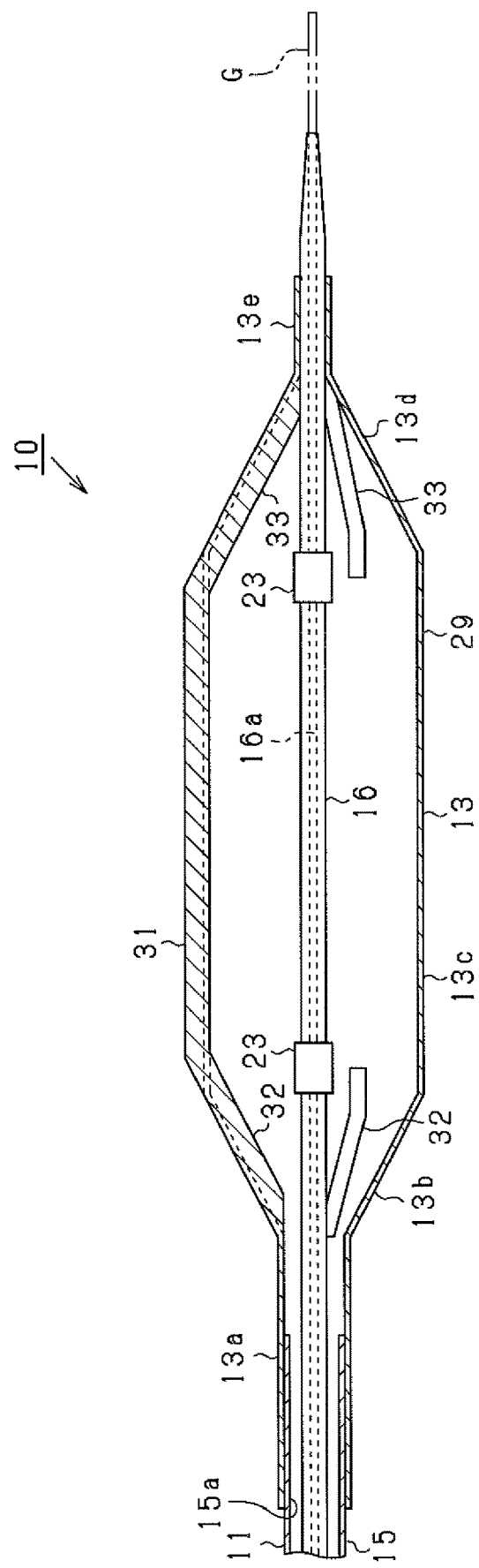
FIG. 2 is a side view of a balloon in an inflated state and a vicinity thereof, showing the balloon and an outer tube in a longitudinal cross section.
Figure 3A:
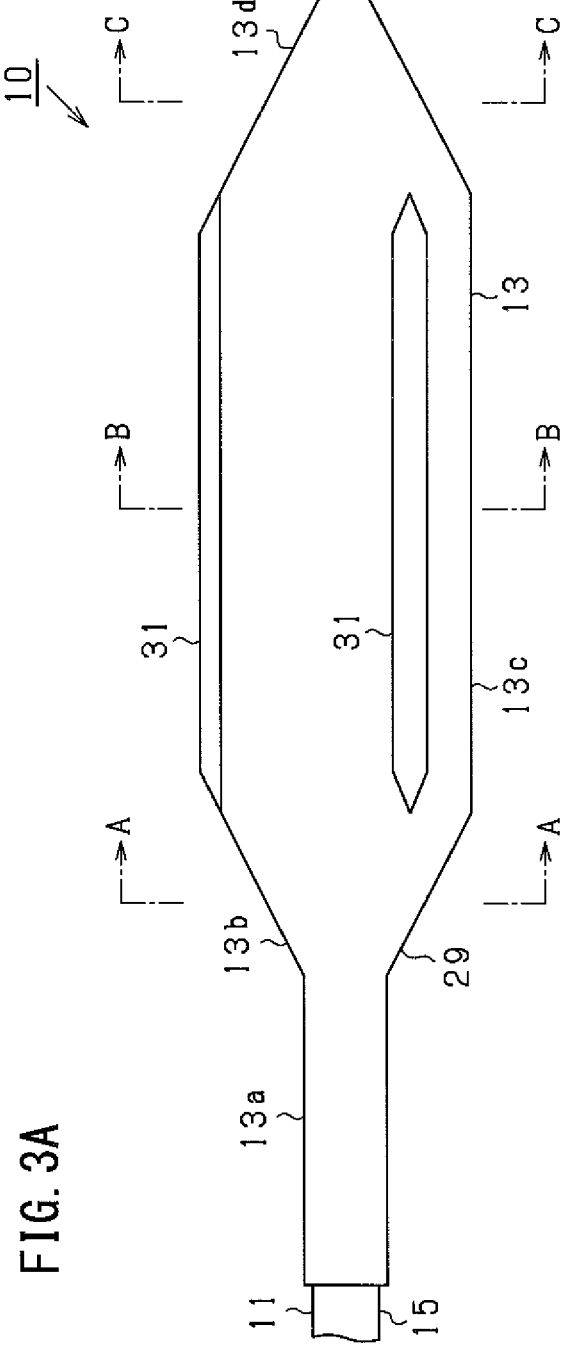
FIG. 3A is a side view showing a configuration of the balloon in the inflated state and the vicinity thereof.
Figure 3D:
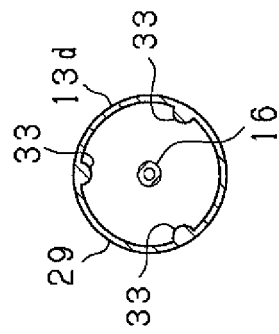
FIG. 3D is a cross sectional view taken along a C-C line in FIG. 3A.
Figure 3C:
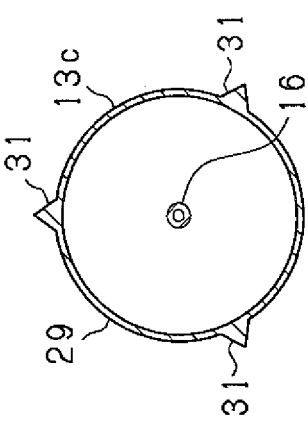
FIG. 3C is a cross-sectional view taken along a B-B line in FIG. 3A.
Figure 3B:
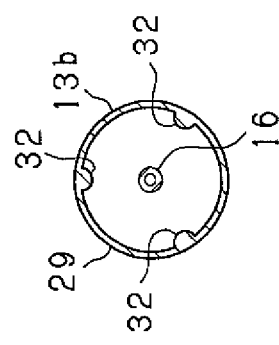
FIG. 3B is a cross sectional view taken along an A-A line in FIG. 3A.
Figure 4A:
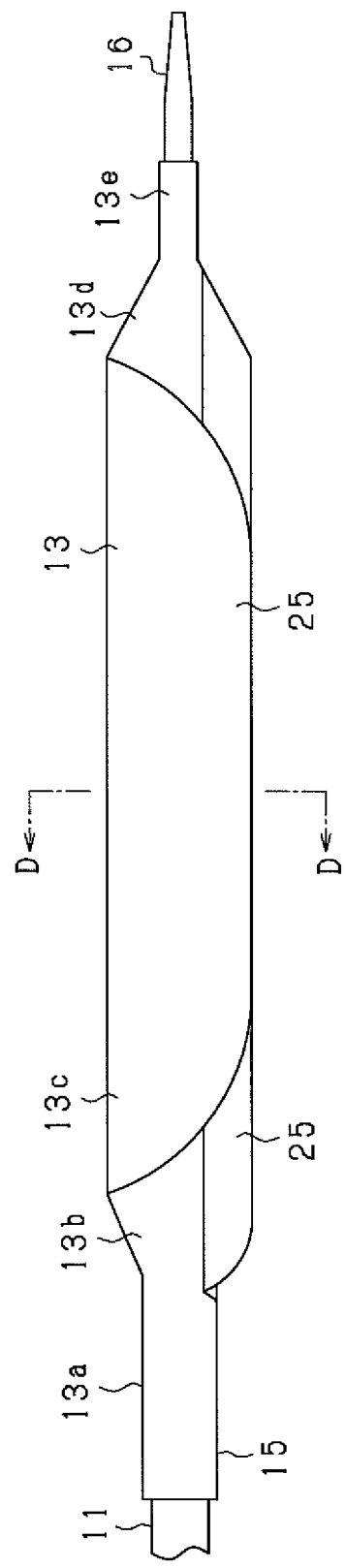
FIG. 4A is a side view showing a configuration of the balloon in a deflated state and the vicinity thereof and FIG. 4B is a cross sectional view taken along a D-D line in FIG. 4A.
Figure 4B:
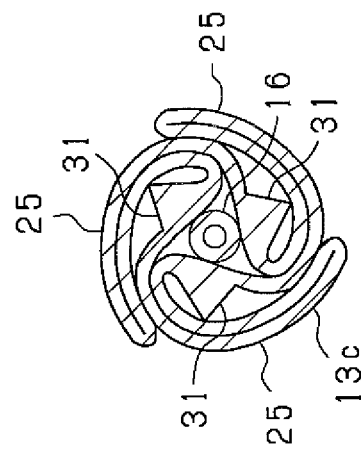

Next, a configuration of the balloon 13 and a vicinity thereof will be described on the basis of FIG. 2 to FIGS. 4A-4B. FIG. 2 is a side view of the balloon 13 in an inflated state and the vicinity thereof, showing the balloon 13 and the outer tube 15 in a longitudinal cross section. FIG. 3A is a side view showing a configuration of the balloon 13 in the inflated state and the vicinity thereof, FIG. 3B is a cross sectional view taken along an A-A line in FIG. 3A, FIG. 3C is a cross-sectional view taken along a B-B line in FIG. 3A, and FIG. 3D is a cross sectional view taken along a C-C line in FIG. 3A. FIG. 4A is a side view showing a configuration of the balloon 13 in a deflated state and the vicinity thereof and FIG. 4B is a cross sectional view taken along a D-D line in FIG. 4A.

As described above, the balloon 13 is provided on the inner tube 16, externally covering the extended region extended on the tip-end side relative to the outer tube 15. As shown in FIG. 2 and FIG. 3A, a base-end portion of the balloon 13 is bonded to the tip-end portion of the outer tube 15, while a tip-end portion thereof is bonded to the tip-end side of the inner tube 16.

The balloon 13 is made of a thermoplastic polyamide elastomer. However, the balloon 13 may be formed of any other thermoplastic resin instead of polyamide elastomer as long as the balloon 13 can be favorably inflated and deflated with the supply and discharge of the fluid. For example, it may be formed of polyethylene, polyethylene terephthalate, polypropylene, polyurethane, polyamide, polyimide, polyimide elastomer, silicone rubber, or the like.

The balloon 13 is formed of a film 29 with a predetermined thickness. The balloon 13 includes opposite bonded portions bonded to the catheter body 11 and an inflation/deflation portion provided between the bonded portions and that is to be inflated and deflated. Specifically, the balloon 13 includes: a base-end leg region 13a bonded to the tip-end portion of the outer tube 15; a base-end cone region 13b tapered such that the inner diameter and outer diameter of the balloon 13 are continuously increased toward the tip-end side; a straight tube region 13c having the same inner diameter and outer diameter therethroughout in a length direction and defining a maximum outer diameter region of the balloon 13; a tip-end cone region 13d tapered such that the inner diameter and outer diameter of the balloon 13 are continuously reduced toward the tip-end side; and a tip-end leg region 13e bonded to the tip-end side of the inner tube 16 in this order from the base-end side. In this case, the base-end cone region 13b, the straight tube region 13c, and the tip-end cone region 13d constitute the inflation/deflation portion, while the base-end leg region 13a and the tip-end leg region 13e each constitute the bonded portion.

It should be noted that the straight tube region 13c corresponds to a "straight tube portion", and the tip-end cone region 13d and the base-end cone region 13b each correspond to a "tapered portion".

The balloon 13 is brought into the inflated state when the compressed fluid is supplied into the balloon 13 through the lumen 15a of the outer tube 15 and brought into the deflated state when a negative pressure is applied to the lumen 15a to cause the compressed fluid to be discharged out of the balloon 13. As shown in FIGS. 4A and 4B, the balloon 13 includes a plurality of (in the present embodiment, three) wings 25 formed in the deflated state. These wings 25 are provided at predetermined intervals (in particular, regular intervals) in a circumferential direction of the balloon 13. The wings 25 are formed to extend in the axial direction at the inflation/deflation portion of the balloon 13. In this case, the wings 25 extend across the base-end cone region 13b, the straight tube region 13c, and the tip-end cone region 13d. With the balloon 13 being in the deflated state, these wings 25 are folded in the circumferential direction of the balloon 13, being wrapped around the inner tube 16.

It should be noted that a pair of contrast rings 23 are attached to the inner tube 16 inside the balloon 13. The contrast rings 23 are intended to improve the visibility of the balloon 13 during x-ray projection so that the balloon 13 is easily positioned with respect to a targeted treatment spot.

In the present balloon catheter 10, the film 29 forming the balloon 13 is provided with a projection projecting in a thickness direction and linearly extending along a surface of the film 29. In the present balloon catheter 10, the projection is intended to reinforce the film 29 and, consequently, improve the pressure resistance of the balloon 13. Hereinafter, description will be made on a configuration related to the projection.

As shown in FIG. 2 and FIG. 3A, the film 29 of the balloon 13 is provided with projections 31 to 33 projecting in the thickness direction thereof. These projections 31 to 33 include the projection 31 provided at the straight tube region 13c of the balloon 13 and the projections 32 and 33 provided respectively at the cone regions 13b and 13d. These projections 31 to 33 are each integrated with the film 29.

The projection 31 at the straight tube region 13c projects toward the outside (outer circumferential side) of the balloon 13 as shown in FIG. 3C. The projection 31 extends in an axial direction of the balloon 13 along an outer surface of the film 29 (i.e., an outer surface of the straight tube region 13c), in particular, it extends throughout the straight tube region 13c in the axial direction. A plurality of such projections 31 are provided at predetermined intervals (in particular, regular intervals) in the circumferential direction of the balloon 13; in the present embodiment, three projections 31 are provided. It should be noted that each projection 31 corresponds to an outer projection.

The projections 31 each have a transverse cross section (in particular, a cross section perpendicular to a longitudinal direction of each projection 31) in a triangular shape. The projections 31 are each provided in an orientation where one of the corners thereof projects toward an outer circumferential side (radially outside) of the balloon 13. It should be noted that the projections 31 are each not necessarily in a triangular shape in a transverse cross section but may be in any other shape, such as a semicircular shape or a rectangular shape, in a transverse cross section.

A projection height (in particular, a projection height from the outer surface of the film 29) of each projection 31 is constant substantially throughout the projection 31 in the longitudinal direction. In particular, the projection height of each projection 31 is constant substantially throughout the projection 31 except both end portions thereof in the longitudinal direction. Both end portions of each projection 31 in the longitudinal direction are slanted in the axial direction such that end surfaces thereof are smoothly continuous respectively with an outer circumferential surface of the base-end cone region 13b and an outer circumferential surface of the tip-end cone region 13d, thus making a projection height thereof low. It should be noted that the projection height of each projection 31 may be constant throughout the projection 31 in the longitudinal direction.

It should be noted that at the straight tube region 13c, the film 29 is provided with the projections 31 (i.e., outer projections) projecting outside the balloon 13 while provided with no projection (inner projection) projecting inside the balloon 13.

Out of the projections 32 and 33 of the cone regions 13b and 13d, the projection 32 of the base-end cone region 13b projects toward the inside (inner circumferential side) of the balloon 13 as shown in FIG. 3B. The projection 32 extends in the axial direction of the balloon 13 along an inner surface of the film 29 (i.e., an inner surface of the base-end cone region 13b); in particular, it extends throughout the base-end cone region 13b in the axial direction. A plurality of such projections 32 are provided at predetermined intervals (in particular, regular intervals) in the circumferential direction of the balloon 13; in the present embodiment, three projections 32 are provided. These projections 32 are provided at the same positions as the projections 31 of the straight tube region 13c in the circumferential direction of the balloon 13. It should be noted that each projection 32 corresponds to an inner projection.

The projections 32 each have a transverse cross section (in particular, a cross section perpendicular to a longitudinal direction of each projection 32) in a semicircular shape protruding toward the inside of the balloon 13. However, the projections 32 are each not necessarily in a semicircular shape in a transverse cross section but may be in any other shape, such as a triangular shape or a rectangular shape, in a transverse cross section.

A projection height (in particular, a projection height from the inner surface of the film 29) of each projection 32 is constant substantially throughout the projection 32 in the longitudinal direction. In particular, the projection height of each projection 32 is constant substantially throughout the projection 32 except a base-end portion thereof in the longitudinal direction. An end surface of the base-end portion of each projection 32 extends along the axial direction, thus making a projection height thereof low. Further, a tip-end portion of each projection 32 extends to the base-end portion of the straight tube region 13c, being continuous with the inner surface of the straight tube region 13c. It should be noted that the projection height of each projection 32 may be constant throughout the projection 32 in the longitudinal direction.

The projection height of each projection 32 is larger than the thickness of the film 29. Further, the projection height of each projection 32 is the same (or substantially the same) as the projection height of each projection 31 at the straight tube region 13c. However, the projection height of each projection 32 may be larger or smaller than the projection height of each projection 31. Further, the projection height of each projection 32 may be increased or reduced from the tip-end side (a straight tube region 13c side) of the projection 32 toward the base-end side (a base-end leg region 13a side) thereof.

It should be noted that at the base-end cone region 13b, the film 29 is provided with the projections 32 (i.e., inner projections) projecting inside the balloon 13 while provided with no projection (i.e., outer projection) projecting outside the balloon 13.

The projection 33 of the tip-end cone region 13d projects toward the inside (inner circumferential side) of the balloon 13 as shown in FIG. 3D. The projection 33 extends in the axial direction of the balloon 13 along the inner surface of the film 29 (i.e., an inner surface of the tip-end cone region 13d); in particular, it extends throughout the tip-end cone region 13d in the axial direction. A plurality of such projections 33 are provided at predetermined intervals (in particular, regular intervals) in the circumferential direction of the balloon 13; in the present embodiment, three projections 33 are provided. These projections 33 are provided at the same positions as the projections 31 of the straight tube region 13c in the circumferential direction of the balloon 13; therefore, they are also provided at the same positions as the projections 32 of the base-end cone region 13b. It should be noted that each projection 33 corresponds to the inner projection.

The projections 33 each have a transverse cross section (in particular, a cross section perpendicular to a longitudinal direction of each projection 33) in a semicircular shape protruding toward the inside of the balloon 13. However, the projections 33 are each not necessarily in a semicircular shape in a transverse cross section but may be in any other shape, such as a triangular shape or a rectangular shape, in a transverse cross section.

A projection height (in particular, a projection height from the inner surface of the film 29) of each projection 33 is constant substantially throughout the projection 33 in the longitudinal direction. In particular, the projection height of each projection 33 is constant substantially throughout the projection 33 except a base-end portion thereof in the longitudinal direction. An end surface of the tip-end portion of each projection 33 extends along the axial direction, thus making a projection height thereof low. Further, the base-end portion of each projection 33 extends to the tip-end portion of the straight tube region 13c, being continuous with the inner surface of the straight tube region 13c. It should be noted that the projection height of each projection 33 may be constant throughout the projection 33 in the longitudinal direction.

The projection height of each projection 33 is larger than the thickness of the film 29. Further, the projection height of each projection 32 is the same (or substantially the same) as the projection height of each projection 31 at the straight tube region 13c and the projection height of each projection 32 at the base-end cone region 13b. However, the projection height of each projection 33 may be larger or smaller than the projection heights of each projection 31 and each projection 32. Further, the projection height of each projection 33 may be increased or reduced from the base-end side (a straight tube region 13c side) of the projection 33 toward the tip-end side (a tip-end leg region 13e side) thereof.

It should be noted that at the tip-end cone region 13d, the film 29 is provided with the projections 33 (i.e., inner projections) projecting inside the balloon 13 while provided with no projection (i.e., outer projection) projecting outside the balloon 13.

In the deflated state of the balloon 13, the plurality of wings 25 are formed at the inflation/deflation portion (the straight tube region 13c and the cone regions 13b and 13d) of the balloon 13 and these wings 25 are folded in the circumferential direction of the balloon 13 as described above. In this case, as shown in FIGS. 4A and 4B, the projections 31 of the straight tube region 13c, which are in a one-to-one relationship with the wings 25, are provided inside the folded respective wings 25. This causes the projections 31 to be externally covered by the wings 25 in the deflated state of the balloon 13; in particular, the projections 31 are entirely covered by the wings 25.

Next, description will be made on a manufacturing method of manufacturing the above-described balloon 13.

First, a tubular parison, which is to be made into the balloon 13, is produced by extrusion molding. The tubular parison, which is formed in the shape of a circular tube, has an outer circumferential surface provided with a protruding stripe extending in the axial direction. A plurality of (specifically, three) such protruding stripes, each of which has a triangular transverse cross section, are formed at regular intervals in a circumferential direction of the tubular parison.

Subsequently, the tubular parison is stretched in a length direction and then blow-molded under predetermined conditions using a mold with a cavity corresponding to the shape of the balloon 13. During the blow-molding, the tubular parison is heated to expand within the mold (cavity). The blow-molding causes the tubular parison to be biaxially stretched. Both ends of the stretched tubular parison are then cut, thus completing the manufacturing of the balloon 13.

In this regard, the mold used for the blow-molding is provided with grooves for accommodating the protruding stripes at a portion corresponding to the straight tube region 13c of the balloon 13. Thus, the projections 31 are formed at a portion of the tubular parison for forming the straight tube region 13c by the blow-molding. Meanwhile, the mold is provided with no groove for accommodating the protruding stripes at a portion corresponding to each of the cone regions 13b and 13d of the balloon 13. This causes the protruding stripes to be pressed against the mold to be compressed (crushed) at a portion of the tubular parison for forming each of the cone regions 13b and 13d during the blow-molding. Thus, no projection (outer projection) projecting on an outer circumferential side is formed at the portion of the tubular parison for forming each of the cone regions 13b and 13d. Further, in this case, the crushed protruding stripes project on an inner circumferential side of the tubular parison and, by virtue of such projected portions, the projections 32 and 33 (inner projections) are formed at the respective portions of the tubular parison for forming the cone regions 13b and 13d.

It should be noted that the mold is also provided with grooves for accommodating the protruding stripes at a portion corresponding to each of the leg regions 13a and 13e of the balloon 13. Thus, projections projecting on the outer circumferential side are likewise formed at a portion of the tubular parison corresponding to each of the leg regions 13a and 13e by the blow-molding. These projections are removed by cutting after the blow-molding.

The above is the description of the manufacturing method of the balloon 13. It should be noted that the manufacturing method of the balloon 13 is not necessarily limited to the above-described method but another manufacturing method may be employed.

Next, a brief description will be made on a method of using the balloon catheter 10.

First, a guiding catheter is inserted through a sheath introducer inserted in a blood vessel and a tip-end opening of the guiding catheter is introduced into a coronary ostium. Next, the guide wire G is inserted through the guiding catheter and the inserted guide wire G is introduced from the coronary ostium to a peripheral site via a treatment site such as a narrowed spot.

Subsequently, the balloon catheter 10 is introduced into the guiding catheter along the guide wire G, and the balloon 13 is positioned at the treatment site while a push/pull operation is performed. It should be noted that the balloon 13 is in the deflated state during the introduction of the balloon catheter 10.

Subsequently, a compressed fluid is supplied to the balloon 13 through the lumen 15a of the outer tube 15 from a hub 12 side using a pressurizer. This causes the balloon 13 to be inflated and the inflated balloon 13 stretches the narrowed spot. Further, during the inflation of the balloon 13, the projections 31 provided at the straight tube region 13c of the balloon 13 are pressed against a blood vessel wall and dug into the blood vessel wall. This makes it possible to keep the balloon 13 from slipping off the narrowed spot during the inflation of the balloon 13. Thus, in the present balloon catheter 10, the projections 31 each function as a slip resistance during the inflation of the balloon 13.

After the completion of the stretching of the narrowed spot by the balloon 13, the compressed fluid is discharged out of the balloon 13, causing the balloon 13 to be in the deflated state. Then, the balloon 13 in the deflated state and, consequently, the balloon catheter 10 are pulled out of the body. A series of the operations are thus completed.

It should be noted that while the balloon catheter 10 is introduced through a blood vessel and mainly used for the treatment of the blood vessel such as a coronary artery, a femoral artery, or a pulmonary artery as described above, the balloon catheter 10 is also usable for any other "vessel", such as a ureter and a gastrointestinal tract, in addition to a blood vessel and a "body cavity" in a living body.

The configuration of the present embodiment described above in detail achieves the following excellent effects.

The film 29 is provided with the linear projections 31 to 33 respectively at the straight tube region 13c and the cone regions 13b and 13d of the balloon 13, which makes it possible to reinforce the film 29 substantially throughout the inflation/deflation portion (the above-described regions 13b and 13d). The pressure resistance of the balloon 13 can thus be favorably increased.

Further, with the projections 31 (hereinafter, also referred to as the outer projections 31), which project outside the balloon 13, provided at the straight tube region 13c as described above, each projection 31 can function as a slip resistance during the inflation of the balloon 13.

Further, with the projections 32 and 33 (hereinafter, also referred to as the inner projections 32 and 33), which project inside the balloon 13, provided respectively at the cone regions 13b and 13d, an increase in the outer diameter of each of the cone regions 13b and 13d can be reduced. Thus, in the configuration where the balloon 13 is added with a slip-resistance function, the pressure resistance of the balloon 13 can be favorably increased with a decrease in the passability of the balloon 13 reduced.

Further, with the inner projections 32 provided at the tip-end cone region 13d to reduce an increase in the outer diameter of the tip-end cone region 13d, a decrease in the passability can be favorably reduced in introducing the balloon 13 into the body. In addition, with the inner projection 33 likewise provided at the base-end cone region 13b to reduce an increase in the outer diameter of this region 13b, a decrease in the passability of the balloon 13 can also be favorably reduced in moving the balloon 13 to the base-end side, such as pulling the balloon 13 out of the body.

With the projections 31 of the straight tube region 13c and the projections 32 and 33 of the cone regions 13b and 13d all extending in the axial direction of the balloon 13 along the surface of the film 29, the elongation of the balloon 13 in the axial direction can be reduced during the inflation of the balloon 13 (in particular, the inflation/deflation portion). A balloon length can thus be easily kept constant during the inflation of the balloon 13.

Specifically, the projections 31 to 33 extend throughout the balloon 13 in the axial direction respectively at the straight tube region 13c and the cone regions 13b and 13d, while the projections 31 to 33 are all provided at the same position in the circumferential direction of the balloon. In this case, the projections 31 to 33 are continuously provided in series throughout the inflation/deflation portion in the axial direction. This makes it possible to further reduce the elongation of the balloon 13 in the axial direction during the inflation of the balloon 13. The balloon length can thus be more easily kept constant during the inflation of the balloon 13.

The present invention is not limited to the above-described embodiment but may be implemented, for example, as follows.

(1) In the above-described embodiment, at the straight tube region 13c and the cone regions 13b and 13d, the projections 31 to 33 are provided throughout the respective regions 13b to 13d in the axial direction of the balloon 13. However, at least any of the projections 31 to 33 may be provided only at a part in the axial direction. Even in this case, it is possible to reduce the elongation of the balloon 13 in the axial direction during the inflation of the balloon 13 as long as the projections 31 to 33 extend in the axial direction, so that the balloon length can be easily kept constant during the inflation of the balloon 13.

(2) In the above-described embodiment, the projections 31 to 33 of the straight tube region 13c and the cone regions 13b and 13d are provided such that they all extend in the axial direction of the balloon 13 along the surface of the film 29. However, at least any of these projections 31 to 33 may extend in a direction different from the axial direction. For example, it is likely that any of the projections is provided such that it extends in the circumferential direction of the balloon 13. Specifically, it is likely that the projection is provided such that it extends throughout the balloon 13 in the circumferential direction. In this case, the projection is a ring-shaped (annular) projection.

Further, any of the projections (for example, each projection 31 of the straight tube region 13c) may be provided such that it spirally extends along the axial direction of the balloon 13. Even in these cases, the film can be reinforced and, consequently, the pressure resistance of the balloon 13 can be improved.

(3) In the above-described embodiment, the projections 32 and 33 of the cone regions 13b and 13d are both inner projections projecting inside the balloon 13. However, either one of these projections 32 and 33 may be an inner projection, while the other is an outer projection projecting outside the balloon 13. Even in this case, an increase in the outer diameter of the cone region provided with the inner projection can be reduced, so that the balloon 13 can be improved in pressure resistance with a decrease in the passability thereof reduced.

(4) In the above-described embodiment, the projections 31 of the straight tube region 13c and the projections 32 and 33 of the cone regions 13b and 13d are provided at the same positions in the circumferential direction of the balloon 13. However, the projections 31 of the straight tube region 13c and the projections 32 and of the cone regions 13b and 13d may be provided at different positions in the circumferential direction of the balloon 13.

(5) In the above-described embodiment, the film 29 is provided with the projections 32 (each corresponding to the inner projection) projecting inside the balloon 13 at the base-end cone region 13b, while a projection projecting outside the balloon 13 (i.e., the outer projection) is not provided. In this regard, it is likely that a projection slightly projecting outside the balloon 13 along each projection 32 (inner projection) is formed in the film 29 at the base-end cone region 13b for the reason of manufacturing the balloon 13 or the like. However, even in this case, such a projection has an extremely small height, so that the film 29 can be reinforced with an increase in the outer diameter of the balloon 13 reduced. It should be noted that this also applies to the tip-end cone region 13d.

(6) In the above-described embodiment, the projections 31, which project outside the balloon 13, are provided at the straight tube region 13c of the balloon 13 and the projections 31 are each used as a slip resistance during the inflation of the balloon 13. However, the balloon 13 is provided with none of such projections 31 (slip resistance) in some embodiments. Accordingly, such a balloon with no slip resistance may be provided with an inner projection projecting inside the balloon 13 at the straight tube region 13c. This makes it possible to reduce an increase in the outer diameter at the straight tube region 13c as well as at the cone regions 13b and 13d. The pressure resistance can thus be improved with a decrease in the passability of the balloon further reduced.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

REFERENCE SIGNS LIST

10 . . . balloon catheter, 13 . . . balloon, 13b . . . base-end cone region as tapered portion, 13c . . . straight tube region as straight tube portion, 13d . . . tip-end cone region as tapered portion, 31 . . . projection as outer projection, 32 . . . projection as inner projection, 33 . . . projection as inner projection

What is claimed is:

1. A balloon catheter comprising:
a balloon that is formed of film and comprises an inflation/deflation portion, wherein
the inflation/deflation portion comprises linear projections that project in a thickness direction of the film and extend along outer and inner surfaces of the film,
one of the linear projections is an inner projection that projects from the inner surface of the film toward an inside of the balloon,
the inflation/deflation portion comprises:
an inflatable straight tube portion; and
a pair of tapered portions that are disposed on opposite sides across the straight tube portion in an axial direction of the balloon and are tapered from the straight tube portion outward,
one of the linear projections is an outer projection that projects from the outer surface of the film toward an outside of the balloon,
the outer projection is disposed at the straight tube portion and not at either of the tapered portions,
the inner projection is disposed at one of the tapered portions and not at the straight tube portion,
the outer projection at the straight tube portion and the inner projection at the one of the tapered portions extend in the axial direction of the balloon along the outer and inner surfaces of the film, respectively,
the outer projection at the straight tube portion extends throughout the straight tube portion in the axial direction,
the inner projection at the one of the tapered portions extends throughout the one of the tapered portions in the axial direction, and
the outer projection and the inner projection are disposed at a same position in a circumferential direction of the balloon.

2. A balloon catheter comprising:
a balloon that is formed of film and comprises an inflation/deflation portion, wherein
the inflation/deflation portion comprises linear projections that project in a thickness direction of the film and extend along outer and inner surfaces of the film,
one of the linear projections is an inner projection that projects from the inner surface of the film toward an inside of the balloon,
the inflation/deflation portion comprises:
an inflatable straight tube portion; and
a pair of tapered portions that are disposed on opposite sides across the straight tube portion in an axial direction of the balloon and are tapered from the straight tube portion outward,
one of the linear projections is an outer projection that projects from the outer surface of the film toward an outside of the balloon,
the outer projection is disposed at the straight tube portion and not at either of the tapered portions,
the inner projection is disposed at one of the tapered portions and not at the straight tube portion,
the inner projection is disposed at a tip-end side tapered portion of the one of the tapered portions,
the outer projection at the straight tube portion and the inner projection at the tip-end side tapered portion extend in the axial direction of the balloon along the outer and inner surfaces of the film, respectively,
the outer projection at the straight tube portion extends throughout the straight tube portion in the axial direction,
the inner projection at the tip-end side tapered portion extends throughout the tip-end side tapered portion in the axial direction, and
the outer projection and the inner projection are disposed at a same position in a circumferential direction of the balloon.

3. A balloon catheter comprising:
a balloon that is formed of film and comprises an inflation/deflation portion, wherein
the inflation/deflation portion comprises linear projections that project in a thickness direction of the film and extend along outer and inner surfaces of the film,
one of the linear projections is an inner projection that projects from the inner surface of the film toward an inside of the balloon,
the inflation/deflation portion comprises:
  an inflatable straight tube portion; and
  a pair of tapered portions that are disposed on opposite sides across the straight tube portion in an axial direction of the balloon and are tapered from the straight tube portion outward,
one of the linear projections is an outer projection that projects from the outer surface of the film toward an outside of the balloon,
the outer projection is disposed at the straight tube portion and not at either of the tapered portions,
the inner projection is disposed at one of the tapered portions and not at the straight tube portion,
the inner projection is disposed at a tip-end side tapered portion of the one of the tapered portions,
one of the linear projections is another inner projection that is disposed at the other of the tapered portions,
the outer projection at the straight tube portion and the inner projections at the tapered portions extend in the axial direction of the balloon along the outer and inner surfaces of the film, respectively,
the outer projection at the straight tube portion extends throughout the straight tube portion in the axial direction,
the inner projections of the tapered portions respectively extend throughout the tapered portions in the axial direction, and
the outer projection and the inner projections are disposed at a same position in a circumferential direction of the balloon.

* * * * *